(12) United States Patent
Hornick et al.

(10) Patent No.: US 7,427,662 B2
(45) Date of Patent: Sep. 23, 2008

(54) INHIBITION OF ANGIOGENESIS AND DESTRUCTION OF ANGIOGENIC VESSELS BY APOLIPOPROTEIN A-I AND HIGH DENSITY LIPOPROTEIN

(75) Inventors: Conrad A. Hornick, New Orleans, LA (US); Eugene A. Woltering, Kenner, LA (US)

(73) Assignee: Baord of Supervisors of Louisiana State University And Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 11/047,852

(22) Filed: Feb. 1, 2005

(65) Prior Publication Data

US 2006/0172919 A1    Aug. 3, 2006

(51) Int. Cl.
    *C07K 14/435* (2006.01)
(52) U.S. Cl. .................... 530/359; 530/350; 514/2
(58) Field of Classification Search .......... 530/359, 530/350; 514/2
    See application file for complete search history.

(56) References Cited

U.S. PATENT DOCUMENTS

| 5,059,528 A | 10/1991 | Bollen et al. ........ 439/69.4 |
| 6,258,596 B1 | 7/2001 | Benoit et al. ........ 435/325 |
| 6,743,428 B1 * | 6/2004 | Chang et al. ........ 424/185.1 |

OTHER PUBLICATIONS

Schulter V. (Arteriosclerosis, Thrombosis, and Vascular Biology 21 (3) 433-8, 2001).*
Fruchart, J.C. et al., "Apolipoprotein A-containing lipoprotein particles: physiological role, quantification, and clinical significance," Clin. Chem., vol. 38, pp. 793-797 (1992).
Asztalos, B.F. et al., "Normolipidemic subjects with low HDL cholesterol levels have altered HDL subpopulations," Arterioscler. Thromb. Vasc. Biol., vol. 17, pp. 1885-1893 (1997).
Bicknell, R., "Vascular targeting and the inhibition of angiogenesis," Annals of Oncology, vol. 5, pp. 45-50 (1994).
Creamer, D. et al., "Overexpression of the angiogenic factor platelet-derived endothelial cell growth factor/thymidine phosphorylase in psoriatic epidermis,"Br. J. Dermatol., vol. 137, pp. 851-855 (1997).
Eerola, A.K. et al., "Tumour infiltrating lymphocytes in relation to tumour angiogenesis, apoptosis," Lung Cancer, vol. 26, pp. 73-83 (1999).
Gasparini, G., "The rationale and future potential of angiogenesis inhibitors in neoplasia," Drugs, vol. 58, pp. 17-38 (1999).
Levy, R.I. et al., "The structure, function and metabolism of high-density lipoproteins: A status report," Circulation, vol. 62, pp. IV4-IV8 (1980).
Maniotis, A.J. et al., "Vascular channel formation by human melanoma cells in vivo and in vitro: Vasculogenic mimicry," Am. J. Pathol., vol. 155, pp. 739-752 (1999).
Rosen, L., "Antiangiogenic strategies and agents in clinical trials," Oncologist, vol. 5, supplement 1, pp. 20-27 (2000).
Rupnick, M.A. Rupnick, M.A. et al., "Adipose tissue mass can be regulated through the vasculature," PNAS, vol. 99, pp. 10730-10735 (2002).
Silverman, D.I. et al., "High-density lipoprotein subfractions," Am. J. Med., vol. 94, pp. 636-645 (1993).
Watson, J.C. et al., "Breast cancer increases initiation of angiogenesis without accelerating neovessel growth rate," Surgery, vol. 122, pp. 509-514 (1997).
Wenger, F.A. et al., "Tumor size and lymph-node status in pancreatic carcinoma—is there a correlation to the preoperative function?," Langenbecks Archives of Surgery, vol. 384, pp. 473-478 (1999).
Alaupovic, P, "Significance of Apolipoproteins for Structure, Function, and Classification of Plasma Lipoproteins," Methods in Enzymology, vol. 263, pp. 32-60 (1996).
Cho, K-H et al., "Role of individual amino acids of apolipoprotein A-I in the activation of lecithin:cholesterol acyltransferase and in HDL rearrangements," Journal of Lipid Research, vol. 42, pp. 379-389 (2001).
Fazio, S. et al., "Apolipoprotein AI as therapy for atherosclerosis: Does the future of preventive cardiology include weekly injections of the HDL protein?", Molecular Interventions, vol. 3, pp. 436-440 (2003).
Franceschini, G. et al., High density lipoprotein-3 heterogeneity in subjects with the Apo A-1Milano variant, Journal of Biological Chemistry, vol. 257, pp. 9926-9930 (1982).

(Continued)

*Primary Examiner*—David Lukton
(74) *Attorney, Agent, or Firm*—Bonnie J. Davis; John H. Runnels

(57) ABSTRACT

Apolipoprotein A-I-rich Lhigh-density Lipoprotein 2 (HDL2) and Apolipoprotein A-I (ApoA-I) was discovered to inhibit angiogenesis in an in vitro human angiogenesis model, the human placental vein angiogenesis model. Apolipoprotein A-I was able to destroy a pre-existing angiogenic response as well as prevent the development of new vessels. Application of Apolipoprotein A-I will be effective in inhibiting tumor growth dependent on angiogenesis, and in decreasing existing blood vessels formed by tumors. It will also be effective in treating non-cancerous diseases which symptoms include an increase in angiogenesis, e.g., psoriasis, retinopathy of prematurity, neovascular glaucoma, diabetic retinopathy, obesity, and psoriasis.

34 Claims, 8 Drawing Sheets

OTHER PUBLICATIONS

Frank, P.G. et al., "Apolipoprotein A-I: structure-function relationships," Journal of Lipid Research, vol. 41, pp. 853-872 (2001).

Patsch, W. et al., "Apolipoproteins: Pathophysiology and Clinical Implications," Methods in Enzymology, vol. 263, pp. 3-32 (1996).

Roma, P. et al., "In vivo metabolism of a mutant form of apolipoprotein A-1, apo A-1Milano, associated with familial hypoalphalipoprotenemia," Journal of Clinical Investigation, vol. 91, pp. 1445-1452 (1993).

Von Eckardstein et al., "Interaction of reconstituted high density lipoprotein discs containing human apolipoprotein A-I (ApoA-I) variants with murine adipocytes and macrophages," Journal of Biological Chemistry, vol. 268, pp. 2616-2622, (1993).

Ye, S.Q. et al., "Influence of genetic polymorphisms on responsiveness to dietary fat and cholesterol," American Journal of Clinical Nutrition, vol. 72, pp. 1275S-1284S (2000.

* cited by examiner

INHIBITION OF ANGIOGENESIS AND DESTRUCTION OF ANGIOGENIC VESSELS BY APOLIPOPROTEIN A-I AND HIGH DENSITY LIPOPROTEIN

The development of this invention was subject to a contract between the Board of Supervisors of Louisiana State University and Agricultural and Mechanical College, and the United States Department of Veterans Affairs. The Government has certain rights in this invention.

ANGIOGENESIS

In an adult, two types of blood vessels can potentially be found. The normal blood vessel is a resting, quiescent, fully developed vessel. A second form, a proliferating or developing blood vessel, occurs rarely during the normal human life cycle (occurring only in early development and during reproduction, e.g., menstrual cycle and pregnancy). In contrast, the process of angiogenesis, the proliferation and development of new blood vessels, often occurs in wound healing and in pathological processes, e.g., tumor growth. Angiogenesis is a complex process involving many stages, including extracellular matrix remodeling, endothelial cell migration and proliferation, capillary differentiation, and anastomosis. All detectable solid tumors (tumors over 2 mm in diameter, a size reflecting the limit of simple diffusion to supply cells with oxygen and nutrients or to remove wastes) exploit angiogenesis to supply the needed blood to proliferating tumor cells. Studies have demonstrated that the level of vascularization in a tumor is strongly associated with metastasis in melanoma, breast, and lung carcinomas. See R. Bicknell, "Vascular targeting and the inhibition of angiogenesis," Annals of Oncology, vol. 5, pp. 45-50 (1994).

Angiogenesis inhibitors have been suggested to intervene into neoplastic processes. See G. Gasparini, "The rationale and future potential of angiogenesis inhibitors in neoplasia," Drugs, vol. 58, pp. 17-38 (1999). The inhibitory agents block angiogenesis, thereby causing tumor regression in various types of neoplasia. Known therapeutic candidates include naturally occurring angiogenic inhibitors (e.g., angiostatin, endostatin, platelet factor-4), specific inhibitors of endothelial cell growth (e.g., TNP-470, thalidomide, interleukin-12), agents that neutralize angiogenic molecules (e.g., antibodies to fibroblast growth factor or vascular endothelial growth factor), suramin and its analogs, tecogalan, agents that neutralize receptors for angiogenic factors, agents that interfere with vascular basement membrane and extracellular matrix (e.g., metalloprotease inhibitors, angiostatic steroids), and anti-adhesion molecules (e.g., antibodies such as anti-integrin alpha v beta 3). See L. Rosen, "Antiangiogenic strategies and agents in clinical trials," Oncologist, vol. 5, supplement 1, pp. 20-27 (2000).

Pathogenic angiogenesis occurs when improper control of angiogenesis causes either excessive or insufficient blood vessel growth. Excessive blood vessel proliferation in cancer-related conditions favors tumor growth and development of distant metastases. In other diseases, it is the root cause of tissue injury, including blindness associated with proliferative retinopathies, skin disorders such as psoriasis, and rheumatoid arthritis. Diseases that have been associated with neovascularization include, for example, Crohn's disease, diabetic retinopathy, macular degeneration, obesity, corneal neovascularization, malignant tumor growth beyond 2 mm, benign tumors, benign functional endocrine tumors, hemangioma, arterial/venous malformations, sickle cell anemia, sarcoidosis, syphilis, pseudoxanthoma elasticum, Pagets disease, vein occlusion in the eye, infections of the retina, primary hyperparathyroidism, secondary hyperparathyroidism, tertiary hyperparathyroidism, artery occlusion, carotid obstructive disease, chronic uveitis/vitritis, mycobacterial infections, Lyme disease, systemic lupus erythematosis, psoriasis, retinopathy of prematurity, Eales disease, Bechets disease, infections causing retinitis or choroiditis, presumed ocular histoplasmosis, Bests disease, myopia, optic pits, Stargarts disease, pars planitis, chronic retinal detachment, hyperviscosity syndrome, toxoplasmosis, trauma, rheumatoid arthritis, and post-laser laser complications. Other angiogenic-related diseases may include, for example, diseases associated with rubeosis (neovascularization of the angle), and diseases caused by abnormal proliferation of fibrovascular or fibrous tissue, including all forms of proliferative vitreoretinopathy. Any disease having a known angiogenic counterpart could potentially be treated with an anti-angiogenic factor, e.g., psoriasis. See D. Creamer et al., "Overexpression of the angiogenic factor platelet-derived endothelial cell growth factor/thymidine phosphorylase in psoriatic epidermis," Br. J. Dermatol., vol. 137, pp. 851-855 (1997).

Angiogenesis is a prominent contributor to solid tumor growth and the formation of distant metastases. Several experimental studies have concluded that primary tumor growth, tumor invasiveness, and metastasis all require neovascularization. The process of tumor growth and metastasis is complex, involving interactions among transformed neoplastic cells, resident tissue cells (e.g., fibroblasts, macrophages, and endothelial cells), and recruited circulating cells (e.g., platelets, neutrophils, monocytes, and lymphocytes). A possible mechanism for the maintenance of tumor growth is an imbalance, or disregulation, of stimulatory and inhibitory growth factors in and around the tumor. Disregulation of multiple systems allows the perpetuation of tumor growth and eventual metastasis. Angiogenesis is one of many systems that is disregulated in tumor growth. In the past it has been difficult to distinguish between disregulation of angiogenesis and disregulation of other systems affecting a developing tumor. Another complicating factor is that aggressive human melanomas mimic vasculogenesis by producing channels of patterned networks of interconnected loops of extracellular matrix, in which red blood cells, but not endothelial cells, are detected. See A. J. Maniotis et al., "Vascular channel formation by human melanoma cells in vivo and in vitro: Vasculogenic mimicry," Am. J. Pathol., vol. 155, pp. 739-52 (1999). These channels may facilitate perfusion of tumors, independent of perfusion from angiogenesis.

A tumor cannot expand beyond approximately 2 mm without a blood supply to provide nutrients and remove cellular wastes. Tumors in which angiogenesis is important include solid tumors, and benign tumors including acoustic neuroma, neurofibroma, trachoma, and pyogenic granulomas. Inhibiting angiogenesis could halt the growth and potentially lead to regression of these tumors. Angiogenic factors have been reported as being associated with several solid tumors, including rhabdomyosarcoma, retinoblastoma, Ewing sarcoma, neuroblastoma, and osteosarcoma.

Angiogenesis has also been associated with some non-solid tumors, including blood-born tumors such as leukemias, various acute or chronic neoplastic diseases of the bone marrow marked by unrestrained proliferation of white blood cells, usually accompanied by anemia, impaired blood clotting, and enlargement of the lymph nodes, liver, and spleen. It is believed that angiogenesis may play a role in the abnormalities in the bone marrow that give rise to leukemias and multiple myelomas.

Anti-angiogenic factors inhibit tumor growth beyond 2 mm by inhibiting the angiogenic response and thus inhibiting blood vessel growth to the tumor. Although angiogenesis in a tumor may begin at an early stage, a tumor requires a blood supply to grow much beyond about 2 mm. Up to 2 mm diameter, tumors can survive by obtaining nutrients and oxygen by simple diffusion. Most anti-angiogenic factors are not cytotoxic, i.e., capable of killing the tumor cells directly. Small tumors of a size about 1 $mm^3$ can be effectively inhibited and destroyed by factors, either endogenous or exogenous, that stimulate the immune system. It is generally accepted that once a tumor has reached a critical size, the immunological system is no longer able to effectively destroy the tumor; i.e., there is a negative correlation between tumor size and immune competence. See A. K. Eerola et al., "Tumour infiltrating lymphocytes in relation to tumour angiogenesis, apoptosis," Lung Cancer, vol. 26, pp. 73-83 (1999); and F. A. Wenger et al., "Tumor size and lymph-node status in pancreatic carcinoma—is there a correlation to the preoperative immune function?," Langenbecks Archives of Surgery, vol. 384, pp. 473-478 (1999). Early adjuvant use of an effective anti-angiogenic agent to preclude development of tumor metastases beyond 1 to 2 $mm^3$ may allow more effective tumor attack and control by the body's immunological mechanisms. In addition, prolonged adjuvant use of a non-toxic angiogenic inhibitor may prevent tumor dissemination by blocking the growth of vessels required for the transport of tumor cells that would form metastatic foci.

Angiogenesis has also been implicated in obesity. Several mice strains, both young and aged animals, used as obesity models treated with anti-angiogenic agents lost weight. See M. A. Rupnick et al., "Adipose tissue mass can be regulated through the vasculature," PNAS, vol. 99, pp. 10730-10735 (2002). This same study also found that adipose tissue mass was reduced by the anti-angiogenic compounds.

New anti-angiogenic factors are needed, in particular, compounds that not only inhibit new angiogenic growth, but also that degrade existing capillary networks. Very few anti-angiogenic factors have been reported to diminish existing capillary networks.

LIPOPROTEINS

In human plasma four major circulating lipoproteins have been named: cylomicrons (CM), very low-density lipoproteins (VLDL), low-density lipoproteins (LDL), and high-density lipoproteins (HDL). HDL is involved in the removal of cholesterol from peripheral tissues by transporting it to the liver or to other lipoproteins.

HDL are synthesized de novo in both the liver and small intestine as protein-rich disc-shaped particles. The primary apoproteins of HDL are apoA-I, apoA-II, apoC-I, apoC-II, and apoE. Newly formed HDL contain very little cholesterol and cholesteryl esters. HDL are converted from their initial discoidal shape into spherical lipoprotein particles through the accumulation of cholesteryl esters in the neutral core of the lipoprotein particle. Cholesterol is accumulated by HDL from chylomicron remnants VLDL remnants (also called intermediate density Lipoproteins or IDL) and directly from cell surface membranes. The cholesterol is esterfied through the action of an HDL-associated enzyme lecithin:cholesterol acyltransferase ("LCAT"). For LCAT to transfer a fatty acid from lecithin (phosphatidylcholine) to the C-3-OH group of cholesterol, interaction with ApoA-I found on the HDL surface is required. This accumulation of core cholesteryl esters converts nascent HDL to $HDL_2$ and $HDL_3$. See R. I. Levy et al., "The structure, function and metabolism of high-density lipoproteins: A status report," Circulation, vol. 62, pp. IV4-8 (1980); and D. I. Silverman et al., "High-density lipoprotein subfractions," Am. J. Med., vol. 94, pp. 636-45 (1993).

HDL are usually isolated from the plasma by ultracentrifugation. The normal HDL density range is from 1.063 g/mL to 1.21 g/mL, which divides roughly into two ranges HDL2 (1.063 g/mL to 1.125 g/mL) and HDL3 (1.125 g/mL to 1.21 g/mL). More recently, two major populations of particles in HDL have been identified by two dimensional electrophoresis followed by immunoblotting and enzyme-linked differential anitbody immunosorbent assay. One of these populations contains particles with apoA-I alone, and the other contains particles with both apoA-I and apoA-II. The relative proportion of apoA-I particles is highest in the HDL2 fraction, while HDL3 is more a combination of apoA-I and apoA-II. See J. C. Fruchart et al., "Apolipoprotein A-containing lipoprotein particles: physiological role, quantification, and clinical significance," Clin. Chem., vol. 38, pp. 793-7 (1992); and B. F. Asztalos et al., "Normolipidemic subjects with low HDL cholesterol levels have altered HDL subpopulations," Arterioscler. Thromb. Vasc. Biol., vol. 17, pp. 1885-1893 (1997).

Human apolipoprotein A-I (ApoA-I) is the major protein constituent of HDL and lymph chylomicrons. ApoA-I is primarily synthesized in the liver and small intestine as a precursor protein (preproapo A-I). Preproapo A-I is cleaved intracellularly to form proapo A-I, the form secreted into the plasma and lymph. In the plasma, six amino acids are cleaved from proapo A-I to form mature ApoA-I.

Mature ApoA-I is a single unglycosylated polypeptide composed of 243 amino acids of known sequence. ApoA-I serves as a cofactor of a plasma enzyme (lecithin: cholesterol acyltransferase), responsible for the formation of most cholesterol esters in plasma. Decreased levels of ApoA-I may result in disorders of the plasma lipid transport system and in the development of coronary heart disease. Low levels of both ApoA-I and HDL has been shown to be a strong risk factor for heart attacks and other atherosclerotic vascular diseases. See U.S. Pat. Nos. 5,059,528 and 6,258,596.

We have discovered Apolipoprotein A-I-rich High-density Lipoprotein 2 (HDL2) and Apolipoprotein A-I (ApoA-I) inhibited angiogenesis in an in vitro human angiogenesis model, the human placental vein angiogenesis model. Moreover, Apolipoprotein A-I was able to destroy a pre-existing angiogenic response as well as prevent the development of new vessels. Application of Apolipoprotein A-I or HDL2 will be effective in inhibiting tumor growth dependent on angiogenesis, and in decreasing existing blood vessels formed by tumors. It will also be effective in treating non-cancerous diseases which symptoms include an increase in angiogenesis, e.g., psoriasis, retinopathy of prematurity, neovascular glaucoma, diabetic retinopathy, rheumatoid arthritis, obesity, and psoriasis.

EXAMPLE 1

Materials and Methods

Figure 1A:
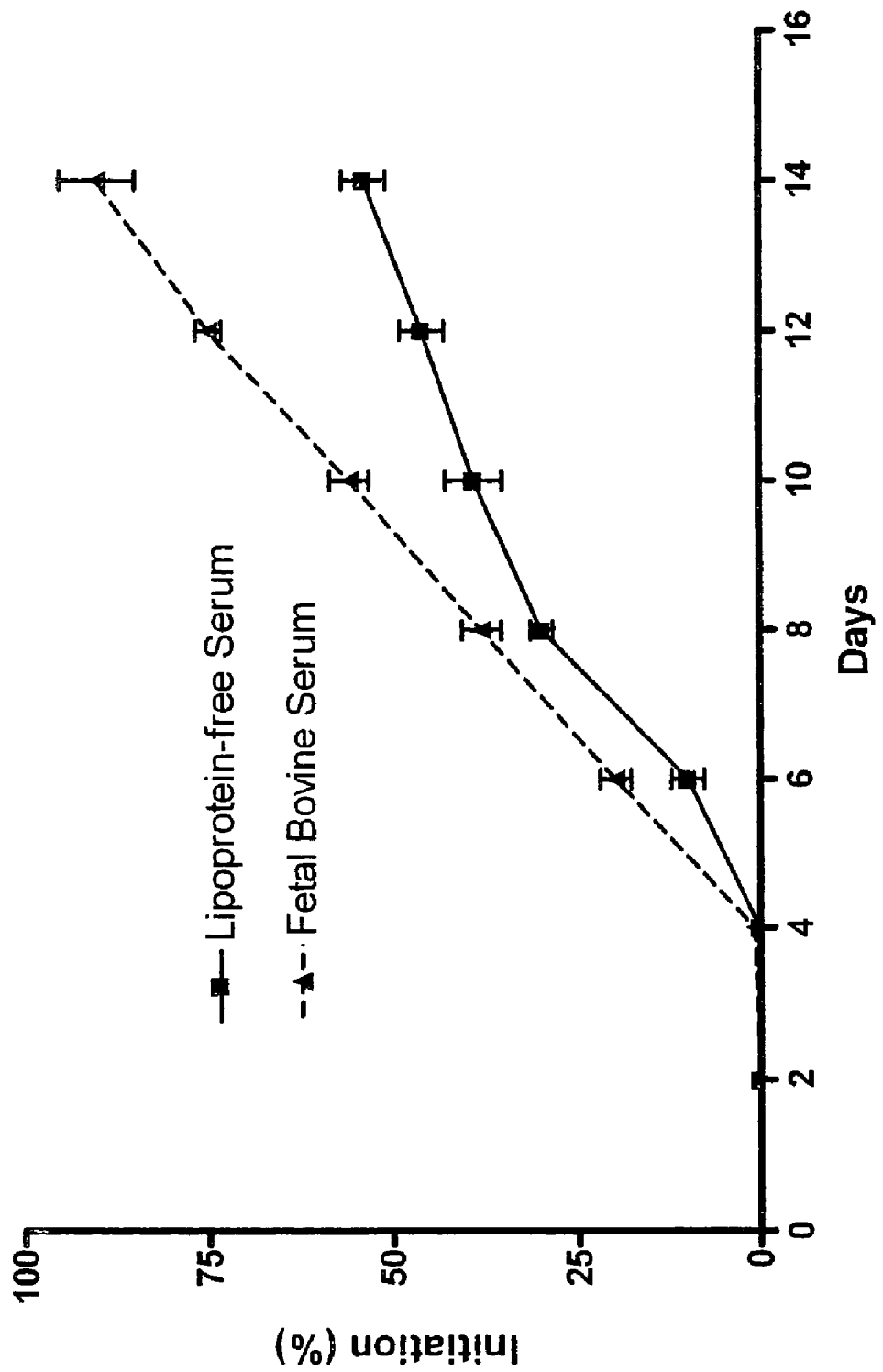
FIG. 1a illustrates the effect of a lipoprotein-free serum and normal serum (fetal bovine serum) on the initiation of angiogenesis in human placental vein discs.

The Human Placental Vein Angiogenesis Model: Discarded human placentas were anonymously obtained with prior approval of an Institutional Review Board. The placental veins were dissected free from the placenta and adventitial tissue. The trimmed vein segment was opened longitudinally to produce a flat film of full thickness of venous tissue. Vein discs (2 mm diameter) were created with a sterile skin punch (Miltex Instrument Company, Inc., Lake Success, N.Y.). The discs were placed into wells of a standard 96-well plate (Corning Inc., Corning, N.Y.). The vein disc harvest was completed within three hours of delivery to optimize endothelial cell viability. An effort was made to use adjacent discs taken from a segment of individual placental veins in both the control and treatment groups. Each well was preloaded with a human thrombin solution (0.05 IU in 2.0 µl) and allowed to evaporate to dryness before use. All chemicals are from Sigma Chemical Company (St. Louis, Mo.), unless otherwise indicated.

Following the placement of the 2 mm vein disc in the bottom of each thrombin-containing well, the disc was covered with 100 µl of a clot-forming media, comprising 0.3% fibrinogen and 0.5% ε-amino caproic acid dissolved in Human Placental Vein Angiogenesis Media (HPVAM). HPVAM is made of Medium 199 (Vitrogen Corporation, Carlsbad, Calif.), and an antibiotic/antimycotic solution (50 U/ml penicillin, 50 U/ml streptomycin sulfate, and 3.75 µg/ml amphotericinβ; Vitrogen Corporation). The fibrin-containing medium clots within 15 min at 37° C. The fibrin gels were overlaid with tissue culture medium comprising Minimum Essential Medium (MEM) (Gibco, Green Island, N.Y.), and then supplemented with serum (with or without lipoproteins) and other experimental compounds. In previous experiments, the radial outgrowth of capillary-like tubules was immunohistochemically stained for von Willebrand's factor and identified as endothelial in origin. (Data not shown).

Source of Liproprotein-free Serum (LPS), Very Low-density Lipoprotein (VLDL}, Low Denisty Lipoprotein (LDL), and High-density Lipoprotein (HDL). Lipoproteins were separated from nomorlipidemic serum obtained from volunteers by density adjustment of the sera by adding 1.21 g/ml KBr and then by ultracentrifugation in a Beckman 50.2 Ti rotor in an L-8 ultracentrifuge for 48 hr at 130,000×g. The lipoprotein fraction is collected from the top and removed with a standard tube slicing apparatus. The remaining serum is lipoprotein-free. Individual lipoproteins are harvested in a similar fashion with serial ultracentrifugation by removing VLDL at a density of 1.006 g/ml with 18 hr centrifugation; LDL at a density of 1.063 g/ml with 24 hr centrifugation; and HDL at a density of 1.21 g/ml with 48 hr centrifugation. KBr was removed from the lipoprotein and LPS fractions by dialysis against 0.15 M NaCl.

Evaluation of Angiogenesis: Visual evaluation of all wells was performed at 20× or 40× magnification with a standardized reference grid by an unbiased observer using an inverted microscope. Every other day, discs were graded using two criteria: the initiation of sprouting (initiation) and the degree of sprouting or response (angiogenic index). Initiation of an angiogenic response was defined as the development of five or more vessel sprouts of at least 0.2 mm length around the periphery of the vein disc. Initiation occurred in 50-95% of the wells, usually 4 to 6 days after establishment of the clots. Initiation, i.e., the number of wells that indicated an angiogenic response, was expressed as a percent of the total wells plated.

The angiogenic index (AI) was defined using a subjective visual rating system. Each disc was visually rated for the development of vessel sprouting in all four quadrants. The quadrants of each disc were rated on a 0-4 scale, depending on the number of sprouts (density) and the length of sprouts. Scores for all four quadrants were summed to give the AI for that disc. The AI was a numerical rating that could range from 0 to 16. A score of zero indicated no vessel growth in any of the four quadrants, while a score of 16 indicated long, dense angiogenic vessel growth in all four quadrants. For most experiments, the AI is expressed as a mean plus/minus standard deviation. A zero AI indicated that no initiation occurred in that disc. This lack of initiation could have been due either to the effect of the experimental compound or to the vein disc not being angiogenic. In previous experiments, we have shown that only a small percent, about 2 to 3%, of vein discs are not angiogenic. (data not shown)

EXAMPLE 2

Effect of Lipoprotein-Free Serum on Angiogenic Growth and Initiation

The placental vein discs (PVD) were used to test the effects of a lipoprotein-free serum on angiogenic growth and initiation. Media 199 was supplemented with fetal bovine serum (FBS) or with Lipoprotein-free Serum (LPS) isolated as described in Example 1. Every two days for 14 days, the medium in each well was replaced, and the vein discs were scored for both initiation of angiogenesis and for an angiogenic index. Three placentas were used, and 30 replicates in both lipoprotein-free and control groups.

Figure 1B:
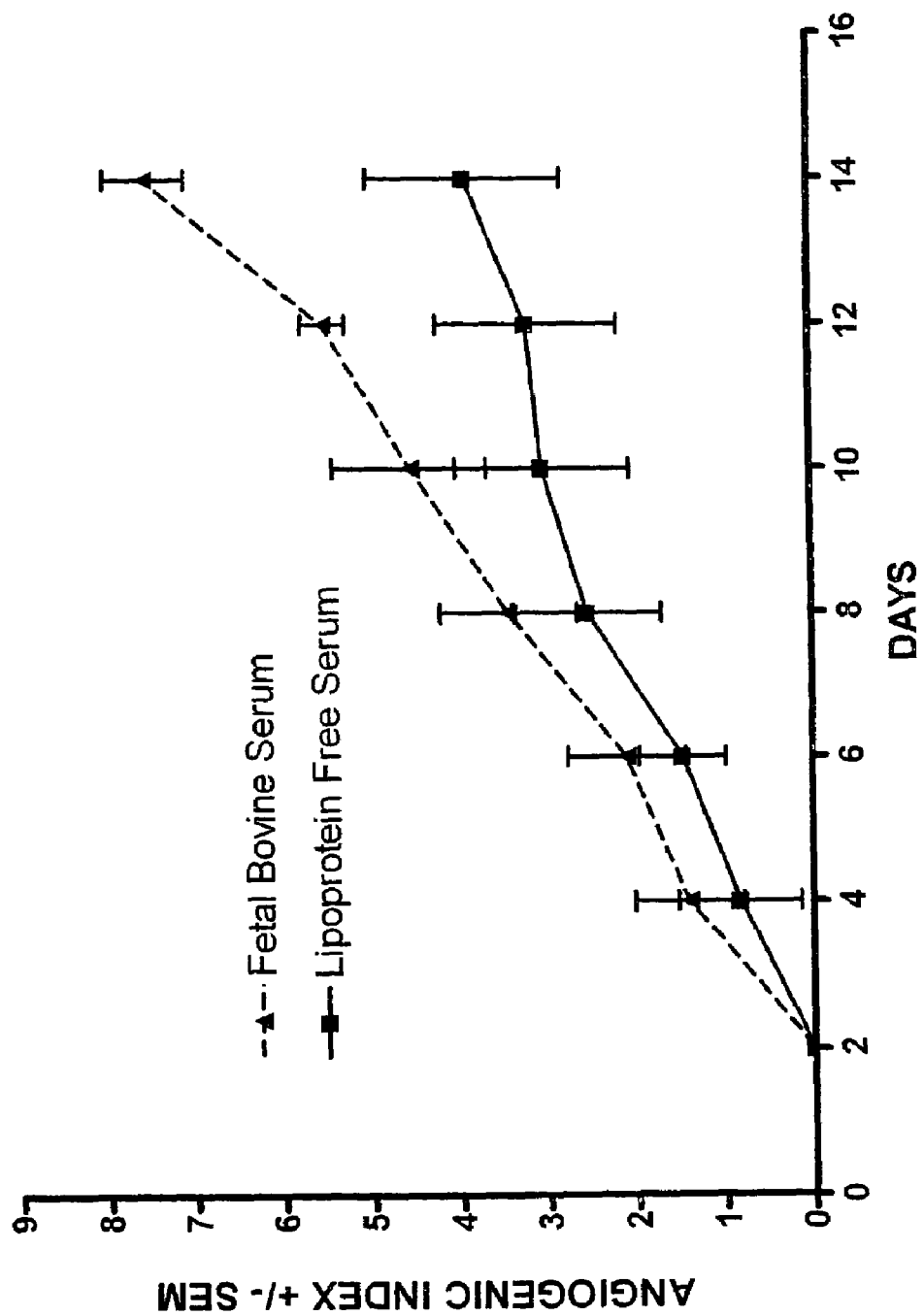
FIG. 1b illustrates the effect of a lipoprotein-free serum and normal serum (fetal bovine serum) on angiogensis (both initiation and proliferation) in human placental vein discs as measured by an angiogenic index.

As shown in FIGS. 1a and 1b, both the initiation of angiogenesis and the angiogenic index was reduced in the LPS experimental group. This experiment indicated that lipoproteins are necessary for the full angiogenic response.

EXAMPLE 3

Effects of Various Lipoprotein Species on Angiogenic Growth and Initiation

PVD were used to test the effects of various plasma lipoprotein species on angiogenic growth and initiation. PVD were grown in Media 199 with 20% FBS alone (control), or with the addition of one of the following lipoproteins at a concentration of 20%: VLDL, LDL, or HDL. The lipoprotein species were isolated as described in Example 1. Every two days for 14 days, the medium in each well was replaced, and the vein discs were scored for both initiation of angiogenesis and angiogenic index. Data are derived from a minimum of sixty samples taken from each of three placentas.

Figure 2A:
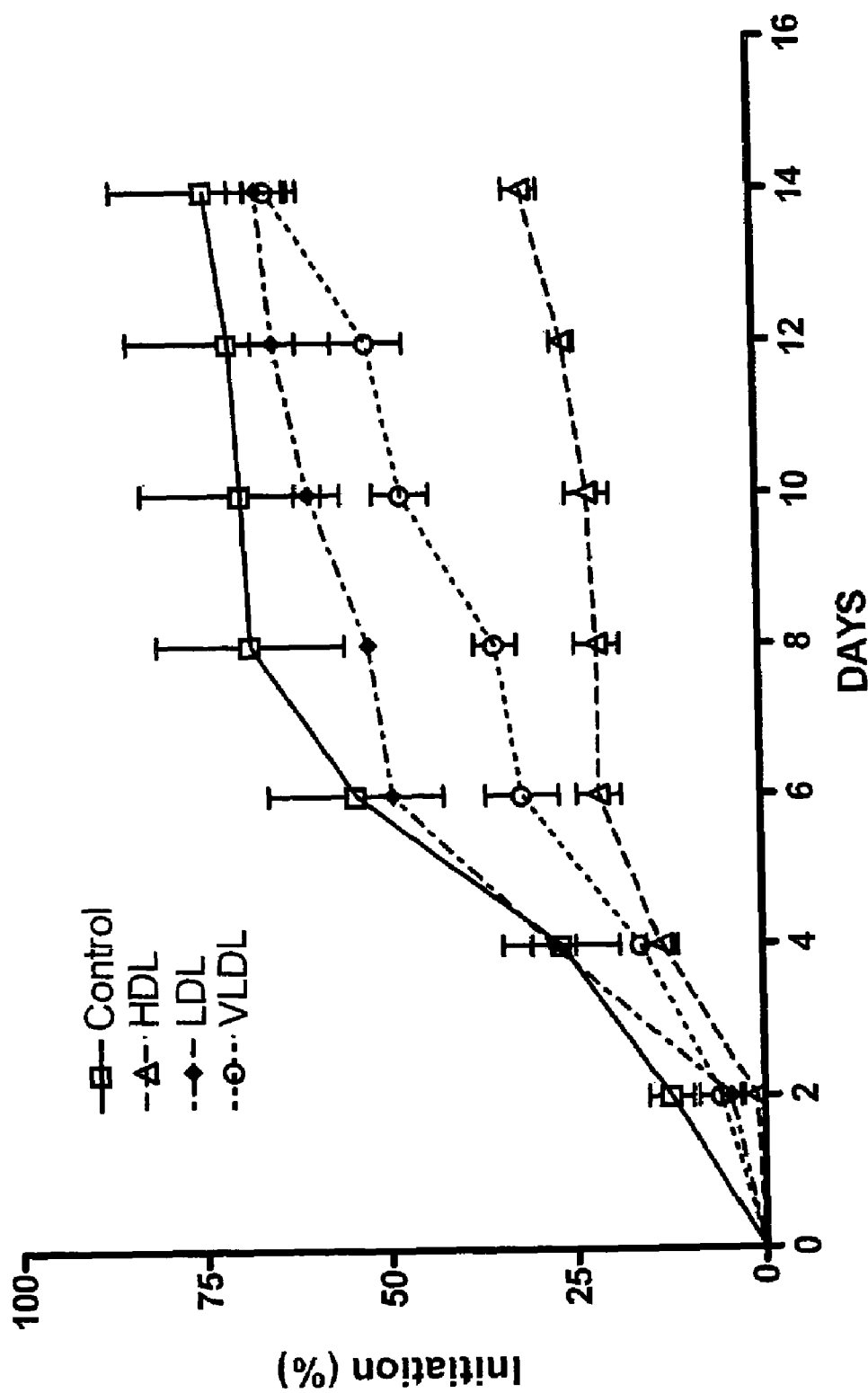
FIG. 2a illustrates the effect of very low-density lipoproteins (VLDL), low-density lipoproteins (LDL), high-density lipoproteins (HDL), and fetal bovine serum (control) on the initiation of angiogenesis in human placental vein discs.
Figure 2B:
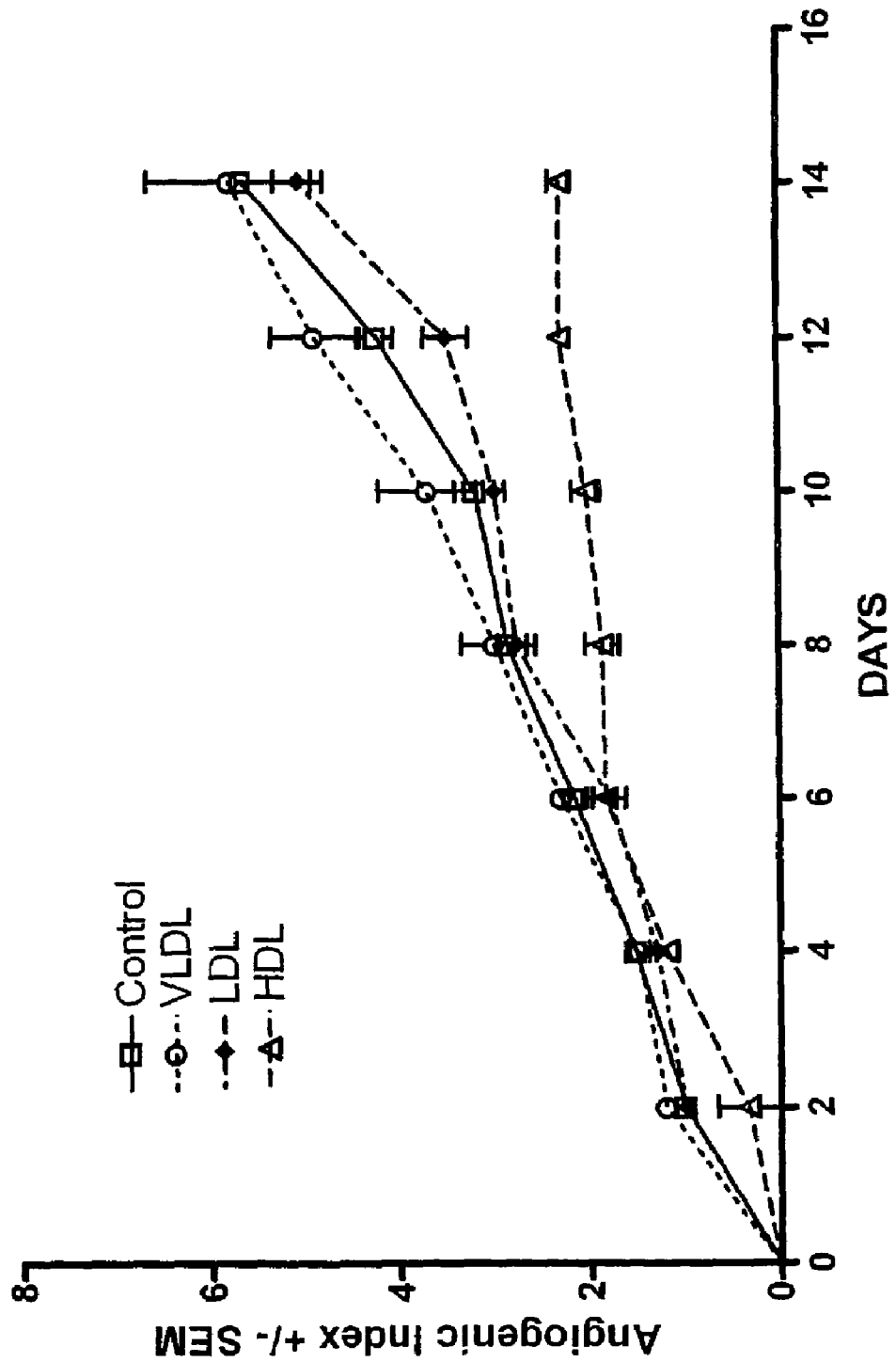
FIG. 2b illustrates the effect of very low-density lipoproteins (VLDL), low-density lipoproteins (LDL), high-density lipoproteins (HDL), and fetal bovine serum (control) on angiogensis (both initiation and proliferation) in human placental vein discs as measured by an angiogenic index.

FIG. 2a illustrates that the initiation of angiogenesis in both VLDL and LDL was approximately equal to that of the control. Only the HDL fraction showed an inhibitory effect. A similar result was seen in the angiogenic index data, i.e., the mean AI of HDL was lower than the other treatments. See FIG. 2b.

EXAMPLE 4

Effects of HDL2 and HDL3 on Angiogenic Growth and Initiation

PVD were used to test for the effects of HDL2 and HDL3, subfractions of HDL, on angiogenic growth and initiation. The PVD (in sets of 30) were grown in Media 199 with 20% FBS alone, or supplemented with the addition of LPS, HLD2 (0.5 mg/ml), or HDL3 (0.5 mg/ml). HDL2 and HDL3 were isolated by ultracentrifugation from the blood of healthy, normolipidemic volunteers. The density range for HDL2 is from about 1.063 g/mL to about 1.125 g/mL, and for HDL3 from about 1.125 g/mL to about 1.21 g/mL. Every two days for 14 days, the medium in each well was replaced, and the vein discs were scored for both initiation of angiogenesis and angiogenic index.

Figure 3:
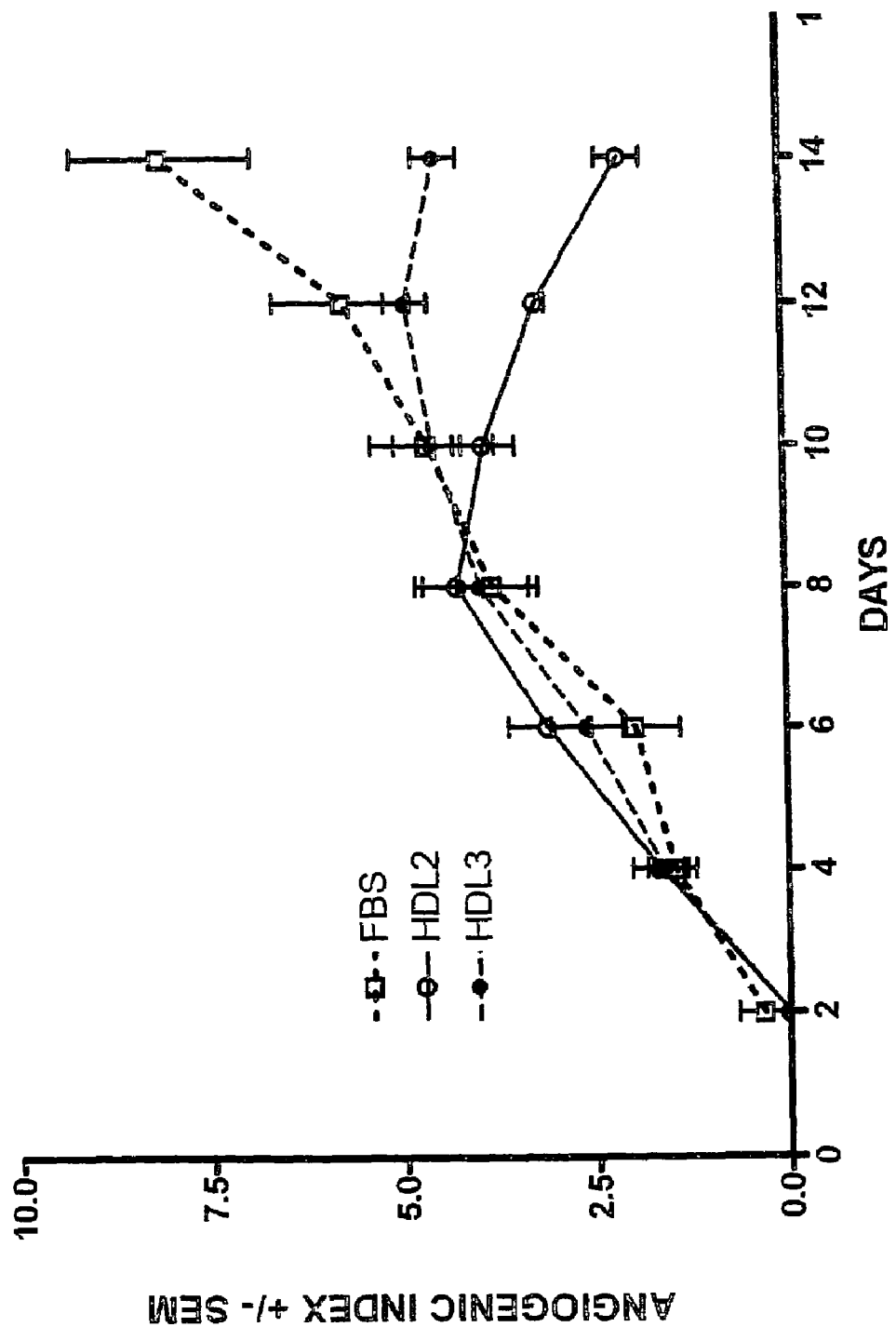
FIG. 3 illustrates the effect of HDL2, HDL3, and fetal bovine serum (FBS) on angiogensis (both initiation and proliferation) in human placental vein discs as measured by an angiogenic index.

The initiation of angiogenic growth, as measured by the percent angiogenesis in the wells, was not affected by any of the treatments in this experiment (Data not shown). However, as shown in FIG. 3, both HDL2 and HDL3 caused a drop in the mean AI, indicating an inhibition of angiogenic proliferation. However, HDL2 was much better at inhibiting the angiogenic growth.

EXAMPLE 5

Effects of HDL2 and ApoA-I on Angiogenic Growth and Initiation

PVD were used to test the effects of HDL2 and its primary constituent, apolipoprotein A-I (ApoA-I) on angiogenic growth and initiation. The PVD (in sets of 30) were grown in Media 199 with 20% FBS alone; or supplemented with the addition of HLD2 (0.5 mg/ml); or ApoA-I (0.5 mg/ml). ApoA-I was purchased from Academy Bio-Medical Co. (Houston, Tex.). HLD2 was isolated as described above. Every two days for 14 days, the medium in each well was replaced, and the vein discs were scored for both initiation of angiogenesis and angiogenic index.

Figure 4A:
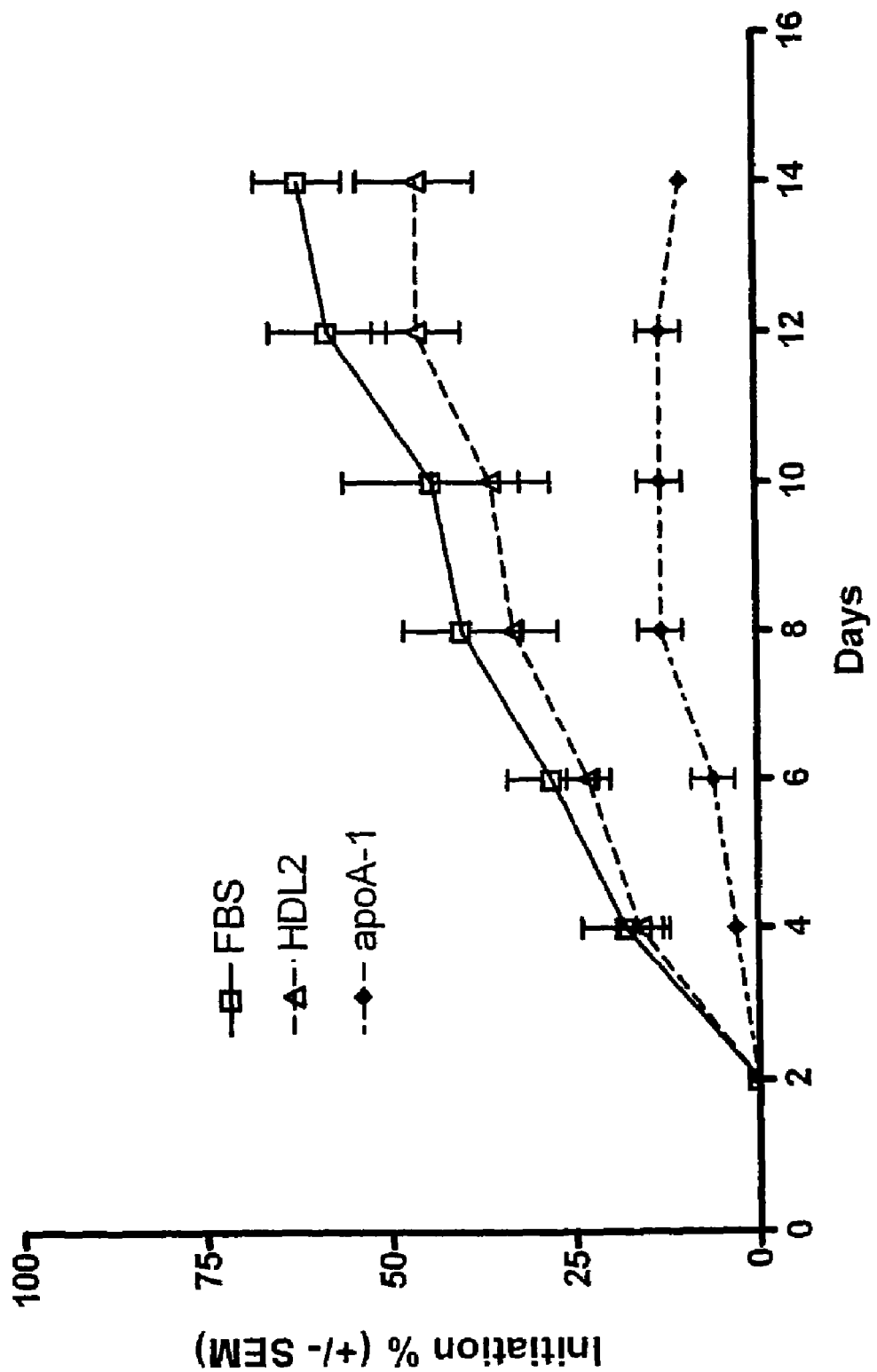
FIG. 4a illustrates the effect of HDL2, human apolipoprotein A-I (ApoA-I), and fetal bovine serum (FBS) on the initiation of angiogenesis in human placental vein discs.
Figure 4B:
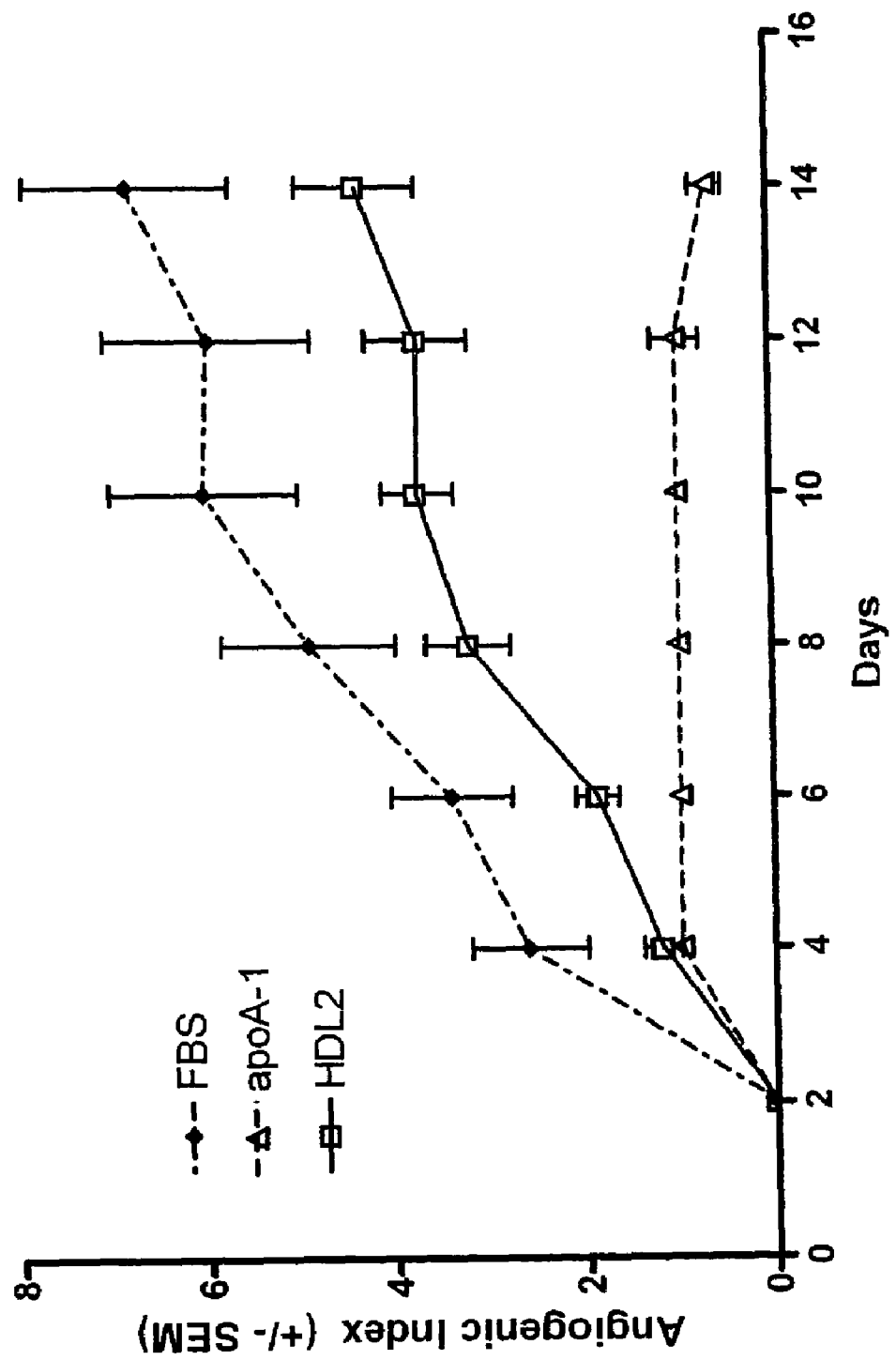
FIG. 4b illustrates the effect of HDL2, human apolipoprotein A-I (ApoA-I), and fetal bovine serum (FBS) on angiogensis (both initiation and proliferation) in human placental vein discs as measured by an angiogenic index.

As shown in FIG. 4a, HDL2 showed a similar drop in the mean AI as seen in Example 3, indicating an inhibition of angiogenic growth. ApoA-I showed a substantially greater reduction than that seen with HDL2. Moreover, as seen in FIG. 4b, ApoA-I also inhibited the initiation of angiogenesis. ApoA-I is a more effective inhibitor of initiation and proliferation of angiogenic vessels.

Without wishing to be bound by this theory, it is believed that the action of ApoA-I is the result of ApoA-I binding to receptors on capillary endothelium and removing cholesterol from developing cells.

EXAMPLE 6

Effect of ApoA-I on Established Angiogenic Vessels

To test the effect of ApoA-I on established capillary networks, a single placenta was used to generate PVDs. The PVD were grown for 6 days, and then two sets of 10 explants were matched for levels of angiogenic growth. Half of the explants were treated with Media 199 with 20% FBS and ApoA-I (0.5 mg/ml); and the other half received media with 20% FBS and an equivalent amount of saline. Every two days for 14 days, the medium in each well was replaced, and the vein discs were scored for both initiation of angiogenesis and angiogenic index.

Figure 5:
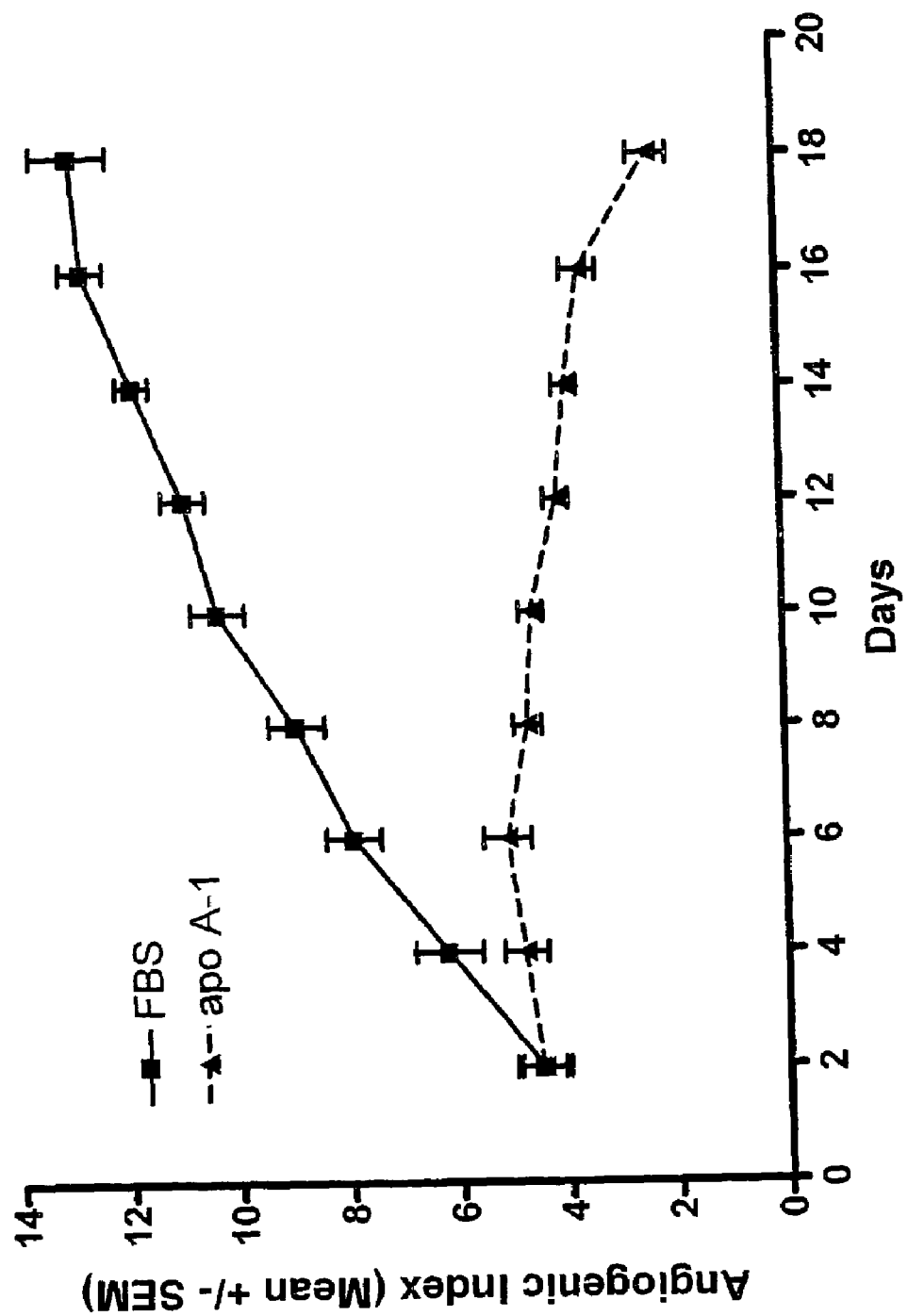
FIG. 5 illustrates the effect of human apolipoprotein A-I (ApoA-I), and fetal bovine serum (FBS) on angiogensis in an established capillary network, a six-day angiogenic growth in human placental vein discs as measured by an angiogenic index.

As shown in FIG. 5, ApoA-I substantially induced dissolution of vessels in an established network. The PVD were stained with MTT, a vital dye, and examined with a microscope. ApoA-I appeared to be inducing apoptosis in the capillary endothelial cells. (Data not shown).

The terms "derivatives" and "analogs" are understood to be particular peptides or proteins, wherein one or more amino acid units have been omitted or replaced by one or more different amino acid units, or wherein one or more functional groups have been replaced by one or more other functional groups, or wherein one or more groups have been replaced by one or several other isosteric groups. In general, the term covers all derivatives of ApoA-I that exhibit a qualitatively similar effect to that of the unmodified peptide. For example, they may be more or less potent than the naturally occurring peptide, bind to a different receptor subtype, or have a longer biologic half-life. The term also covers agonists and antagonists to the naturally occurring peptide that bind the same receptor. For example, ApoA-I$_{Milano}$ is a derivative of ApoA-I. See P. Rome et al., "In vivo metabolism of a mutant form of apolipoprotein A-I, ApoA-I$_{Milano}$, associated with familial hypoalphalipoproteinemia," J. Clin. Invest., vol. 91, pp. 1445-1452 (1993); and G. Franceschini et al., "High density lipoprotein-3 heterogenetiy in subjects with the Apo-AI$_{Milano}$ variant," J. Biol. Chem., vol. 257, pp. 9926-9930 (1982).

The term "therapeutically effective amount" as used herein refers to an amount of either HDL2 or ApoA-I sufficient to either inhibit angiogenesis or to degrade existing capillary networks. The term "therapeutically effective amount" therefore includes, for example, an amount of ApoA-I sufficient to prevent the growth of angiogenic vessels found in diseases of tumor growth, diabetic retinopathy, psoriasis, retinopathy of prematurity, and preferably to reduce by at least 50%, and more preferably to reduce by at least 90%, the amount of angiogensis. The dosage ranges for the administration of HDL2 or ApoA-I are those that produce the desired effect. Generally, the dosage will vary with the age, weight, condition, sex of the patient, type of tumor, and degree of tumor development. A person of ordinary skill in the art, given the teachings of the present specification, may readily determine suitable dosage ranges. The dosage can be adjusted by the individual physician in the event of any complications or adverse reactions occur. In any event, the effectiveness of treatment can be determined by monitoring the extent of angiogenic inhibition or remission by methods well known to those in the field. Moreover, HDL2 or ApoA-I can be applied in pharmaceutically acceptable carriers known in the art.

ApoA-I or HDL2 may be administered to a patient by any suitable means, including parenteral, subcutaneous, intrapulmonary, topically, and intranasal administration. Parenteral infusions include intramuscular, intravenous, intraarterial, or intraperitoneal administration. ApoA-I or HDL2 may also be administered transdermally, for example in the form of a slow-release subcutaneous implant, or orally in the form of capsules, powders, or granules.

Pharmaceutically acceptable carrier preparations for parenteral administration include sterile, aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. The active therapeutic ingredient may be mixed with excipients that are pharmaceutically acceptable and are compatible with the active ingredient. Suitable excipients include water, saline, dextrose, glycerol and ethanol, or combinations thereof. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, inert gases, and the like.

The form may vary depending upon the route of administration. For example, compositions for injection may be provided in the form of an ampule, each containing a unit dose amount, or in the form of a container containing multiple doses.

ApoA-I or HDL2 may be formulated into therapeutic compositions as pharmaceutically acceptable salts. These salts include the acid addition salts formed with inorganic acids such as, for example, hydrochloric or phosphoric acid, or organic acids such as acetic, oxalic, or tartaric acid, and the like. Salts also include those formed from inorganic bases such as, for example, sodium, potassium, ammonium, calcium or ferric hydroxides, and organic bases such as isopropylamine, trimethylamine, histidine, procaine and the like.

Controlled delivery may be achieved by admixing the active ingredient with appropriate macromolecules, for example, polyesters, polyamino acids, polyvinyl pyrrolidone, ethylenevinylacetate, methylcellulose, carboxymethylcellulose, prolamine sulfate, or lactide/glycolide copolymers. The rate of release of the HDL2 or ApoA-I may be controlled by altering the concentration of the macromolecule.

Another method for controlling the duration of action comprises incorporating the ApoA-I or HDL2 into particles of a polymeric substance such as a polyester, peptide, hydrogel, polylactide/glycolide copolymer, or ethylenevinylacetate copolymers. Alternatively, ApoA-I or HDL2 may be encapsulated in microcapsules prepared, for example, by coacervation techniques or by interfacial polymerization, for example, by the use of hydroxymethylcellulose or gelatin-microcapsules or poly(methylmethacrylate) microcapsules, respectively, or in a colloid drug delivery system. Colloidal dispersion systems include macromolecule complexes, nanocapsules, microspheres, beads, and lipid-based systems including oil-in-water emulsions, micelles, mixed micelles, and liposomes.

The present invention provides a method of treating or ameliorating a disease that causes an angiogenic response in the body such as tumors, retinopathy, and psoriasis, comprising administering to a subject displaying symptoms for such disease, a therapeutically effective amount of ApoA-I or HDL2. The term "ameliorate" refers to a decrease or lessening of the symptoms of the disorder being treated. The symptoms that may be ameliorated include those associated with a increase in angiogenesis in the body.

The use of ApoA-I or HDL2 can also be combined with other known antiangiogenic compounds, such as angiostatin, endostatin, platelet factor-4, TNP-470, thalidomide, interleukin-12, antibodies to fibroblast growth factor or vascular endothelial growth factor, tyrosine kinase inhibitors, interferons, suramin and its analogs, tecogalan, and somatostatin and its analogs.

In addition, for tumor treatment, the use of ApoA-I or HDL2 can be combined with neoplastic compounds commonly used in chemotherapy to kill tumor cells, such as paclitaxel or patupilone.

The complete disclosures of all references cited in this specification are hereby incorporated by reference. In the event of an otherwise irreconcilable conflict, however, the present specification shall control.

We claim:

1. A method of ameliorating or inhibiting angiogenesis comprising administering to a mammal in need thereof an effective amount of a compound selected from the group consisting of HDL-2, ApoA-I, and a derivative of ApoA-I, wherein said derivative exhibits a qualitatively similar effect in vivo to that of ApoA-I.

2. The method of claim 1, wherein the compound is ApoA-I.

3. The method of claim 2, wherein the compound is a derivative of ApoA-I.

4. The method of claim 3, wherein the compound is APoA-$I_{Milano}$.

5. The method of claim 1, wherein the compound is HDL-2.

6. The method of claim 1, wherein the angiogenesis is associated with a disease.

7. The method of claim 6, wherein the angiogenic-associated disease is selected from the group consisting of Crohn's disease, diabetic retinopathy, macular degeneration, obesity, corneal neovascularization, malignant tumor growth beyond 2 mm, benign tumors, benign functional endocrine tumors, hemangioma, arterial/venous malformations, sickle cell anemia, sarcoidosis, syphilis, pseudoxanthoma elasticum, Pagets disease, vein occlusion in the eye, infections of the retina, primary hyperparathyroidism, secondary hyperparathyroidism, tertiary hyperparathyroidism, artery occlusion, carotid obstructive disease, chronic uveitis/vitritis, mycobacterial infections, Lyme disease, systemic lupus erythematosis, psoriasis, retinopathy of prematurity, Eales disease, Bechets disease, infections causing retinitis or choroiditis, presumed ocular histoplasmosis, Bests disease, myopia, optic pits, Stargarts disease, pars planitis, chronic retinal detachment, hyperviscosity syndrome, toxoplasmosis, trauma, rheumatoid arthritis, proliferative vitreortinopathy, and post-laser complications.

8. The method of claim 6, wherein the disease is a non-malignant disease.

9. The method of claim 7, wherein the disease is obesity.

10. The method of claim 1, wherein the inhibition of angiogenesis inhibits the growth of a malignant tumor greater than 2 mm in diameter.

11. The method of claim 10, additionally comprising administering an antineoplastic compound.

12. The method of claim 1, wherein said administration is by injection.

13. The method of claim 1, wherein said mammal is a human.

14. The method of claim 9, wherein the inhibition of angiogenesis substantially decreases adipose fat tissue mass.

15. The method of claim 1, additionally comprising administering another antiangiogenic compound.

16. The method of claim 15, wherein the antiangiogenic compound is one or more different compounds selected from the group consisting of ApoA-I, HDL-2, APoA-I$_{Milano}$, angiostatin, endostatin, platelet factor-4, TNP-470, thalidomide, interleukin-12, antibodies to fibroblast growth factor or vascular endothelial growth factor, tyrosine kinase inhibitors, interferons, suramin and its analogs, tecogalan, and somatostatin and its analogs.

17. A method of decreasing the size of an existing capillary network, wherein the growth and maintenance of the network depends on angiogenesis, said method comprising administering to a mammal in need thereof an effective amount of a compound selected from the group consisting of HDL-2, ApoA-I, and a derivative of ApoA-I, wherein said derivative exhibits a qualitatively similar effect in vivo to that of ApoA-I.

18. The method of claim 17, wherein the compound is ApoA-I.

19. The method of claim 17, wherein the compound is a derivative of ApoA-I.

20. The method of claim 19, wherein the compound is APoA-I$_{Milano}$.

21. The method of claim 17, wherein the compound is HDL-2.

22. The method of claim 17, wherein the capillary network is associated with a disease.

23. The method of claim 22, wherein the capillary network-associated disease is selected from the group consisting of Crohn's disease, diabetic retinopathy, macular degeneration, obesity, corneal neovascularization, malignant tumor growth beyond 2 mm, benign tumors, benign functional endocrine tumors, hemangioma, arterial/venous malformations, sickle cell anemia, sarcoidosis, syphilis, pseudoxanthoma elasticum, Pagets disease, vein occlusion in the eye, infections of the retina, primary hyperparathyroidism, secondary hyperparathyroidism, tertiary hyperparathyroidism, artery occlusion, carotid obstructive disease, chronic uveitis/vitritis, mycobacterial infections, Lyme disease, systemic lupus erythematosis, psoriasis, retinopathy of prematurity, Eales disease, Bechets disease, infections causing retinitis or choroiditis, presumed ocular histoplasmosis, Bests disease, myopia, optic pits, Stargarts disease, pars planitis, chronic retinal detachment, hyperviscosity syndrome, toxoplasmosis, trauma, rheumatoid arthritis, proliferative vitreortinopathy, and post-laser complications.

24. The method of claim 22, wherein the disease is a non-malignant disease.

25. The method of claim 23, wherein the disease is obesity.

26. The method of claim 17, wherein the existing capillary network is due to corneal neovascularization.

27. The method of claim 23, wherein the disease is psoriasis.

28. The method of claim 17, wherein said mammal is a human.

29. The method of claim 17, wherein the capillary network is associated with a malignant tumor greater than 2 mm, and wherein decreasing the capillary network decreases the growth and size of said tumor.

30. The method of claim 29, additionally comprising administering an antineoplastic compound.

31. The method of claim 17, wherein the existing capillary network is associated with adipose fat tissue, and wherein decreasing the capillary network decreases the adipose fat tissue.

32. The method of claim 31, wherein the administration is by subcutaneous injection into the fat tissue.

33. The method of claim 17, additionally comprising administering another antiangiogenic compound.

34. The method of claim 33, wherein the antiangiogenic compound is one or more different compounds selected from the group consisting of ApoA-I, HDL-2, APoA-I$_{Milano}$, angiostatin, endostatin, platelet factor-4, TNP-470, thalidomide, interleukin-12, antibodies to fibroblast growth factor or vascular endothelial growth factor, tyrosine kinase inhibitors, interferons, suramin and its analogs, tecogalan, and somatostatin and its analogs.

* * * * *